United States Patent [19]

Blum et al.

[11] Patent Number: 5,885,600

[45] Date of Patent: Mar. 23, 1999

[54] NATURAL INSECT REPELLENT FORMULA AND METHOD OF MAKING SAME

[75] Inventors: Melvin Blum, Wantagh, N.Y.; Michael Roitberg, Highland Park, N.J.

[73] Assignee: Burlington Bio-Medical & Scientific Corp., Farmingdale, N.Y.

[21] Appl. No.: 831,420

[22] Filed: Apr. 1, 1997

[51] Int. Cl.$^6$ ..................................................... A01N 25/02
[52] U.S. Cl. ........................ 424/405; 424/195.1; 426/489
[58] Field of Search .................................... 426/489, 319, 426/418, 419; 424/195.1, 405

[56] References Cited

U.S. PATENT DOCUMENTS

| | | | |
|---|---|---|---|
| 351,897 | 11/1886 | Boyer | 424/405 |
| 3,567,119 | 3/1971 | Wilbert | 424/403 |
| 4,193,986 | 3/1980 | Cox | 424/28 |
| 4,853,413 | 8/1989 | Katz et al. | 514/526 |
| 5,106,622 | 4/1992 | Sherwood et al. | 424/195.1 |
| 5,208,029 | 5/1993 | Plummer et al. | 424/405 |
| 5,240,708 | 8/1993 | Plummer et al. | 424/405 |
| 5,298,251 | 3/1994 | Locke et al. | 424/405 |
| 5,306,497 | 4/1994 | Dunkel et al. | 424/195.1 |
| 5,356,628 | 10/1994 | Locke et al. | 424/405 |
| 5,372,817 | 12/1994 | Locke et al. | 424/405 |
| 5,409,708 | 4/1995 | Locke et al. | 424/410 |
| 5,489,433 | 2/1996 | Aboud | 424/405 |
| 5,518,736 | 5/1996 | Magdassi et al. | 424/451 |

OTHER PUBLICATIONS

Puri et al. Crop Protection 1994 13(1) 45–8 Detergents and plant–derived oils for control of the sweetpotatoe whitefly on cotton.

*Primary Examiner*—Neil S. Levy
*Attorney, Agent, or Firm*—Oliff & Berridge, PLC

[57] ABSTRACT

A composition that has insect repellent properties is made from cold processed extracted oils and an antioxidant, particularly from a combination of Neem, Citronella and Cedarwood oils. The composition can be made into lotions, creams or sprays for application to mammals and vegetation, or it can be formed into polymeric sheets, which in turn can be formed into various useful articles, such as animal collars, garbage bags, or planting material. The polymeric sheets can also be woven into cloth to form clothing, tents and other items. Further, the composition can be hydrogenated to form a semi-solid, which can be made into candles or other wax like substances. The composition is made be extracting the oils and adding an antioxidant, as well as other desired materials. Nitrogen gas may be used to cover the extracted oil before the addition of the antioxidant.

22 Claims, No Drawings

NATURAL INSECT REPELLENT FORMULA AND METHOD OF MAKING SAME

BACKGROUND OF THE INVENTION

1. Field of the Invention

The invention relates to compositions for use in repelling insects. The compositions can be applied to humans, animals, vegetation, or embedded into various materials. Specifically, the insect repellent composition of the invention includes only naturally occurring repellent substances. The invention also relates to special methods for preparing such compositions.

2. Description of Related Art

Insect repellents have been used for centuries to prevent insects from annoying humans and animals alike. Repellents have also been used to prevent insect harm to such items as food, clothing, and furniture. Some examples of known repellents include citronella candles made from citronella oil, and moth balls, which contain chemicals (camphor, para-dichlorobenzene, Napthalene) and/or cedar wood. Over the last century, synthetic chemicals have been developed that more effectively repel insects. Some of these synthetic chemicals include 2-ethyl-3-hexanediol, DDT and DEET (N,N-diethyl toluamide).

However, most synthetic chemical repellents, especially DEET, can be readily absorbed through the skin, causing many accidental poisonings, especially of children. They also can poison wildlife. DDT in particular has been shown to be very harmful to the environment, and DEET is suspected to be a carcinogen, teratogen and/or mutagen. Most of these synthetic chemicals are toxic in certain amounts. Therefore, some states have limited the percentage of synthetic toxic chemicals, especially DEET (e.g. to levels of 10–30%), which may be included in any formulation for human or animal use.

A further concern is that insects can develop a genetic resistance to many synthetic chemicals used in insect repellents and insecticides. Through natural selection, each generation of insect is less effected by any chemical widely used in its area than was the previous generation. Therefore, stronger concentrations or larger amounts of these synthetic chemicals are needed each year in order to control insect populations. In the case of DEET and other synthetic chemicals, particularly known or suspected mutagens, carcinogens and teratogens, these larger doses are undesirable because of the possible deleterious effects on humans, fish, birds, animals and, possibly, vegetation. Further, many of them are nonbiodegradable.

Therefore, another, preferably non-toxic or less toxic, means of repelling insects is desired. Many natural substances are known to repel insects, but these are normally only effective for a short period of time. Further, many natural substances lose their effectiveness when formulated for human or animal use through refining and processing into lotions, oils, sprays and other like substances.

However, it has been found that combinations of various substances that are extracted from vegetable matter by cold processing such as expeller pressing, rolling or centrifugation, for example, form a more effective insect repellent with an efficacy the same as or greater than that of synthetic chemicals such as DEET.

It is known that various naturally occurring substances work as insect repellents and/or insecticides in nature. In particular, the essential oils of various plants repel certain insects and are not believed to cause genetic mutations in insects. Therefore, no resistance to these natural substances should be developed by insects.

These oils can be extracted by many different processes, such as by the use of solvents, steam distillation, use of an expeller, pressurization or centrifugation. However, the processes of solvent extraction and steam distillation are the ones most often used commercially because of their higher yields, lower cost or process simplicity.

One of the most frequently used natural insect repellents is Margosa oil (Neem oil), which yields azadirachtin in large quantities during steam distillation or solvent extraction. Azadirachtin is generally considered desirable for use in large amounts, and is frequently used in insecticide compositions and in low levels for repellency. However, there are some compositions wherein the azadirachtin is removed after solvent extraction, as in U.S. Pat. No. 5,372,817 to Locke et al.

However, many substances that also repel insects other than azadirachtin are present in cold processed extracted oils. For example, other materials yielded from the Margosa (Neem) tree also possess insect repellent properties of equal or greater value than azadirachtin. However, these other substances are not yielded, or are yielded in very small quantities, by the commercially favored processes of steam distillation and solvent extraction.

In contrast, cold expeller pressing, pressurization and ultra-centrifugation yield these substances in large amounts, while often producing less azadirachtin. This is true when performing cold processing extractions on other plants as well—vital substances are recovered by such expeller pressing, pressurization and centrifugation that are otherwise lost in solvent extraction and steam distillation. Temperatures above 60° can destroy many of these active substances.

SUMMARY OF THE INVENTION

The invention uses selective methods such as cold expeller pressing, ultra-centrifugation and cold pressurization to remove those essential oils and factors having insect repellent properties from vegetable matter. Once these essential oils are removed, they are immediately protected from peroxidation, thereby lengthening their shelf life and protecting their active ingredients. They can be protected in an inert environment, such as under a cover of nitrogen gas, until the proper antioxidants are added. It is preferential to process them when possible under an inert atmosphere.

The resultant composition may then be formulated into many different items, such as lotions, sprays and creams for use on humans, animals and vegetation. It may also be formed into polymeric sheets, which can be made into animal collars, planting materials, garbage bags, and the like, or woven into cloth to produce clothing, tents and other such articles with longer term insect repellent properties.

For further effectiveness, additional materials may be added to the composition, such as UV stabilizers or absorbers, surfactants, additional natural oils, and insecticides.

DETAILED DESCRIPTION OF PREFERRED EMBODIMENTS

More than 95% of essential oils commercially sold are usually in the refined state (either solvent processed, filtered, steam distilled or a combination). This is either because of cost or the easy spoilage of the crude oils and their unsightliness due to impure coloration, floating residue and sediments, usually consisting of waxes and gums, which appear to bind or complex with different fractions, and bio-synergists present in the crude oil. Most such oils are also processed at temperatures ranging from 60°–200° C.

However, it is these various fractions and bio-synergists that function as adjunct insect repellents. These essential bio-active ingredients are frequently left behind or destroyed in the common commercially used processes for extracting oils from vegetable matter. The commercial processes generally include steam distillation and solvent extraction.

In contrast, by extracting the oils by means of cold expeller pressing, rolling or centrifugation, for example, the essential ingredients are also extracted from the vegetable matter, yielding an oil with superior insect repellent properties. For example, some of the essential ingredients found in Neem oil are various fractions of limonoids, terpenes and terpenoids such as nimben, salannin, and nimbiol, present in the Azadirachta Indica (Neem) tree and its leaves, bark and seeds. Some of the bio-chemicals, which are more numerous in the crude cold pressed oil than in the refined oil, are meliantriol, nimbinin, nimbidin, nimbidol, thionimone, nimatone, nimidol, nimbedic acid, nimbedinic acid, neo-nimbidin, nimidinin, gedunim, vapinin, meldenin, and vilasinin, as well as certain phyto sterols like beta sitosterol, kaemferol, and some flavanoids such as quercetin and myricetin. Further, azadirachtin has numerous homologs remaining in the crude pressed oil that do not seem to carry over as well when solvent extracted or heated. They are azadirone, azadiradione, beta hydroxy azadiradione, and delta epi azadiradione. By themselves, these bio-chemicals may not have the same bio-activity or insecticidal properties as azadirachtin, but together they show superior effectiveness as insect repellents. The effectiveness can be further improved by combining the bio-chemicals with other crude cold expeller pressed or ultra-centrifuged essential oils and ingredients that also possess insect repellent properties. In particular, it is most effective to combine Neem oil with Citronella oil and Cedarwood oil processed in the same manner.

The crude cold expeller pressed oil of Citronella contains citral, citronellal, limonene, geraniol, linalool, dipentene and pentinoids, and, just like Neem oil, when it is processed by solvent extraction, usually with hexane, some of these are lost, destroyed, oxidized, polymerized or diminished.

Cedarwood oil acts as a repellent due to the various cedar terpenes, cedral and camphors present in it. It is very difficult to find commercial expeller or cold pressed oil of cedar because the most abundant way to extract the oil from the bark, leaves and wood of cedar trees is by steam distillation. Ultra centrifugation has been used to produce pilot quantities of a cold processed oil, which insures that all of the bio-active ingredients, both identifiable and unknown, are retained in the oil and work synergistically, perhaps even catalytically, in repelling most biting insects.

Pure cold processed crude Neem oil has the same degree of repellent effectiveness as a 30% DEET formula. When combined with the other crude expeller pressed oils in a formula containing two parts cold processed Neem oil (50%), one part cold processed Citronella oil (25%) and one part cold processed Cedarwood oil (25%) by total weight of the oils, the effectiveness of this combination, as far as repellency, increases to a duration of time from 2 hours to 3 to 6 hours, depending on factors such as age, sex, temperature, humidity, pH, etc. Generally, formulations may include Neem oil in an amount of from about 10–50% by weight, Citronella oil in an amount of from about 5–30% by weight, and Cedarwood oil in an amount of from about 5–30% by weight. However, quantities of the constituent components outside of these ranges can be used in embodiments.

The composition of this invention is made by extracting these essential oils from vegetable matter by cold expeller pressing, rolling, centrifugation, or like means, and adding an antioxidant to the extracted, crude essential oils. The essential oils are protected from peroxidation before the addition of antioxidants by keeping them in an inert atmosphere, such as by covering them with nitrogen gas. It is important to prevent peroxidation in order to preserve the bio-active ingredients of the crude cold processed essential oils. Processing temperatures are usually from about 5° C. to about 35° C.

An antioxidant formula combining Ethoxyquin with butylated hydroxyanisole (BHA) and/or TBHQ (tertiary butyl hydroquinone) is added in percentages ranging from about 0.01% to about 0.5% in the final composition. Other antioxidants that can also be used are butylated hydroxytoluene (BHT), propyl or dodecyl gallate, dilauryl dithiopropionate or ascorbyl palmitate. If no antioxidant is added to the essential oil or the final composition, the essential oil slowly coalesces and loses its efficacy over time, most likely due to oxidation, precipitation and/or polymerization. Lifetime and efficacy are preserved by factors of ten times or more when antioxidants, and, in particular, the above antioxidant formula, are incorporated into the final composition as early as possible.

The Parabens, Imidureas, Quats and other similar preservatives that are typically used in cosmetics prevent bacterial and fungal growth when added to the composition, but they do not control the lipid oxidation process and subsequent rancidity that result without the antioxidant formula or antioxidants.

The standard solvents of choice for use in the present invention are any light vegetable oil such as cottonseed, soy or rice bran oil, or a very light mineral oil, which emulsifies better. However, other suitable solvents may also be used in embodiments. It is preferred that the antioxidant formula be added to the solvent as well as to the essential oils.

Non-ionic surfactants may also be added to the essential oil composition or the essential oils themselves. Suitable non-ionic surfactants include polyethylene glycol (PEG), oleates, stearates, laurates, and like substances. The addition of a suitable surfactant allows the formulation of a concentrate that can be added to water to form an emulsion that lasts for about 10 to 20 minutes before settling. Shaking easily re-emulsifies the mixture. The dilution ratio of this emulsion ranges from about 1:25 up to about 1:100 parts concentrate to water. The emulsion can then be sprayed on plants, trees, shrubs, grasses, fruits, vegetables, etc., for its insect repellent properties. The period of efficacy can be up to one month. This same emulsion also functions as a dormant oil and anti-transpirant, and it appears to be non-phytotoxic.

Rather than surfactants, other ingredients as known to one of ordinary skill in the art may be added to the essential oil composition to form lotions, sprays and other like carriers for use on animals and humans. These formulations are designed to repel insects such as mosquitoes, fleas, lice, ticks, gnats, chiggers and biting flies (horse, green and black). The combination of essential oils by themselves, as well as repelling insects, also seems to aid in reducing the swelling or itching from insect bites, sun and windburn when applied afterwards.

Other ingredients may be added to increase the efficacy of the essential oil composition, including thymol or oil of thyme, peppermint oil, menthol, camphor, garlic oil (allyl sulfide), wintergreen oil (methyl salicylate), oil of pennyroyal (pulegone), oleoresin capsicum, and other like substances. However, taken alone, these substances have minimal effect. Further, thymol may be used more as an antioxidant then to increase the effectiveness of the essential oil composition.

UV absorbers or stabilizers may also be added in order to preserve these cold pressed oils against the potential harmful effects of sunlight. Further, the addition of UV absorbers forms a combination sunscreen/insect repellent. Some useful UV absorbers or stabilizers are benzophenones, salicylate esters, cinnamate esters, p-aminobenzoic acid (PABA) esters, and the like.

Besides direct application of the composition to animals, humans and vegetation, the composition of the present invention may also be polymerized, allowing a range of products with insect repellent properties to be made. For example, the essential oil composition may be added to an epoxidized soy or castor oil used as a plasticizer. This mixture is then added to a polymer such as polyethylene, eventually producing a polyethylene film containing 0.5 to 1.0% of the active oil ingredients, preferably in a 50/25/25 ratio of Neem oil, Citronella oil and Cedarwood oil. Alternatively, the mixture can also be added to other polymers such as polypropylene and polyolefins, which would require different plasticizers such as polyvinyl chloride/polyvinyl alcohol (PVC/PVA) copolymers, adipates, azelates, chlorinated hydrocarbons, other epoxidized oils, glycolates, pentaerythritol esters, phthalates (butyl benzyl phthalate (BBP), diisodecyl phthalate (DIDP), diisooctyl phthalate (DIOP), dioctyl phthalate (DOP)), polymeric esters, sebacates and tricresyl phosphate. The polymerized composition can then be incorporated into various plastics.

The plastic films of the composition of the present invention increase the effectiveness of the composition by providing resistance to water and the elements. The effectiveness of the plastic films may last up to one year. Up to a 5% concentration of the composition may be incorporated into plastic films, although lesser or greater amounts may be used in embodiments.

These impregnated plastic films can be used, for example, as dog or cat collars, as well as collars for horses and livestock. They may also be used in mats, rugs, and bedding materials for the above animals. The plastic films, particularly using polyolefins, can be woven into hats, jackets or tents for hunters, fishermen and other sportsmen. The impregnated plastic films can also be formed into insect repellent garbage bags.

For gardening, plastic flower pots can be manufactured that would possess long term insect repellency. The plastic films could be wrapped around trees, shrubs or bushes, or laid out as strips on the ground over newly planted seeds or seedlings.

Further, the essential oil composition of cold pressed oils in particular can be hydrogenated into a semi-solidified state, allowing the formation of insect repellent candles and the like. The essential oil composition may also be added to a liposome, wax, resin, latex or polymeric time release composition to further enhance its lifetime.

The various possible compositions can be used in a pump spray, roll on applicator, aerosol, pressure sprayer, fogger, ultrasonic mister, or applied directly as an oil solution or creamy lotion. They can be formed into waxed or plastic balls, pellets, and the like for use as a highly effective long term moth repellent as a safer replacement for naphthalene or para-dichloro benzene (PDB).

Additionally, the composition can be added to waxes, paints, urethanes and varnishes to apply to floors and furniture to repel insects from these surfaces and, in particular, to prevent them from laying their eggs. By adding the composition to wood shavings or sawdust, clays, vermiculite, diatomaceous earth and the like, a repellent bedding material can be created to use in pet cushions, stockyards, stalls, barns, litter boxes or on the floors of steak houses.

The insect repellent effect of the above described invention results from utilizing only cold pressed oils in their natural state, and protecting them from oxidation as soon as possible.

The effect can be changed from a repellent to an insecticide by adding numerous oil soluble insecticides, such as synthetic pyrethroids, methomyl, Phosmet, dimethyl dichlorovinyl phosphate (DDVP), chlorpyrofos and the like.

The various compositions work effectively against arachnids (spiders, ticks, mites), caterpillars, cockroaches, silver fish, moths, slugs, bees, yellow jackets, beetles, aphids, meal bugs, green flies, horse flies, gnats, mosquitoes, and chiggers. They are, however, ineffective as repellents against fire ants and Carpenter ants unless much larger quantities are used.

The following examples are representative of some formulations that may be made based on the above disclosure. Those practiced in the art will recognize other various formulations and materials that are effective in achieving the invention disclosed herein.

EXAMPLES

A composition combining cold processed Neem, Citronella and Cedarwood oil (50/25/25) was diluted to 20% to 35% into formulated lotions or light mineral oil as the solvent carrier. These formulations were then compared to a similar percentage DEET product with comparable efficacy results. Lotions and creams as per the following formulas were equally effective against comparable DEET products containing 15 to 20% DEET. It is believed that DEET is absorbed more readily into the skin than the lotion or gel formulations of the invention, thus shortening the efficacy period of DEET formulations.

| INSECT REPELLENTS FOR HUMANS AND ANIMALS | |
| --- | --- |
| Formula A - Lotion | |
| Water Phase | |
| Water | 53.73% |
| Pemulen TR-2 | 0.2% |
| Propylene Glycol | 2.0% |
| Hampene 100S | 0.3% |
| Methyl Paraben USP | 0.2% |
| Triethanolamine (TEA) | 0.17% |
| Oil Phase | |
| Cold pressed oil mixture Neem, Citronella, Cedarwood with 0.1% Ethoxyquin/BHA | 35.0% |
| Propyl Paraben USP | 0.1% |
| Arlacel 165 | 3.0% |
| Dow Fluid 344 | 1.0% |
| Titanium Dioxide | 4.0 |
| Germall 11 (Diazolidinylurea) | 0.3% |
| Formula B - Gel | |
| Dioctyl Maleate | 10% |
| Propyl Paraben | 0.1% |
| Cedarwood Oil (Expeller Grade) | 5% |

-continued

| | |
|---|---|
| Neem Oil (Expeller Grade) | 10% |
| Citronella Oil (Expeller Grade) | 5% |
| Ethoxyquin/BHA | 0.1% |
| Geahlene 750 | Balance ~ 69.8% |

INSECT REPELLENT FOR PLANTS, TREES, FRUITS AND VEGETABLES

Formula C - Oil/Water Emulsion Concentrate

| | |
|---|---|
| Cedarwood oil (Expeller pressed) | 5% |
| Margosa oil (Expeller pressed) | 10% |
| Citronella Oil (Expeller pressed) | 55 |
| Ethoxyquin/BHA | 0.1% |
| PEG Dioleate (Polyethylene Glycol) | 3.5% |
| Light Mineral Oil | 76.4% |

The emulsifiable concentration of Formula C is subsequently added to water in 1:25 to 1:50 ratios.

Expeller pressed Lemongrass oil can be substituted for Citronella oil in any of the formulas without detracting from the efficacy. Ethoxyquin phosphate may be used in place of Ethoxyquin in conditions utilizing water or alcohol. Ethoxyquin phosphate possesses even greater antioxidant properties than does base Ethoxyquin.

What is claimed is:

1. A composition for use as an insect repellent comprising:
   a) oils extracted from vegetable matter by a means selected from expeller cold pressing, ultra-centrifugation and the application of pressure, wherein said extraction is conducted at temperatures less than or equal to 35° C.; and
   b) an antioxidant;
      wherein said composition has insect repellent or insecticidal properties, and
      wherein said oils are Neem oil, Citronella oil, and Cedarwood oil, wherein Neem oil is present in a range of from about 10–50%, Citronella oil is present in a range of from about 5–30%, and Cedarwood oil is present in a range of from about 5–30% by total weight of said oils, and said oils are present in a ratio of from 2/1/1 to 5/3/3 Neem/Citronella/Cedarwood.

2. The composition of claim 1, wherein the oils are cold expeller pressed.

3. The composition of claim 1, wherein the oils are present in a ratio of 2/1/1 Neem/Citronella/Cedarwood.

4. The composition of claim 1, further comprising a solvent.

5. The composition of claim 4, wherein the solvent comprises a light oil.

6. The composition of claim 5, wherein the light oil contains the antioxidant.

7. The composition of claim 5, wherein the light oil is a light vegetable oil or a light mineral oil.

8. The composition of claim 7, wherein the light vegetable oil is selected from the group consisting of cottonseed, soy and rice bran oil.

9. The composition of claim 1, further comprising a preservative.

10. The composition of claim 9, wherein the preservative is selected from the group consisting of Parabens, Imidureas and Quaternary Ammonium Compounds.

11. The composition of claim 1, further comprising a surfactant.

12. The composition of claim 11, wherein the surfactant is selected form the group consisting of polyethylene glycols, oleates, stearates, and laurates.

13. The composition of claim 1, further comprising a UV stabilizer or absorber.

14. The composition of claim 13, wherein the UV stabilizer or absorber is selected from the group consisting of benzophenones, salicylate esters, cinnamate esters and p-aminobenzoic acid esters.

15. The composition of claim 1, wherein the antioxidant is one or more of butylated hydroxytoluene, propyl gallate, dodecyl gallate, dilauryl dithiopropionate and ascorbyl palmitate.

16. The composition of claim 1, wherein the antioxidant comprises a mixture of Ethoxyquin or Ethoxyquin Phosphate and one or more of butylated hydroxyanisole and Tertiary Butyl Hydroquinone.

17. The composition of claim 1, wherein the antioxidant is added in an amount of from about 0.01–0.50% by weight of the composition.

18. A method of making the composition of claim 1, comprising:
   a) extracting oil from vegetable matter by a means selected from cold expeller pressing, ultra-centrifugation and the application of pressure; and
   b) adding an antioxidant to the oil.

19. The method of claim 18, further comprising the step of covering the oil with nitrogen gas before adding the antioxidant.

20. The composition of claim 1, further comprising a bio-chemical selected from the group consisting of meliantriol, nimbinin, nimbidin, nimbidol, thionimone, nimatone, nimidol, nimbedic acid, nimbedinic acid, neonimbidin, nimidinin, gedunim, vapinin, meldenin, and vilasinin.

21. The composition of claim 1, further comprising a bio-chemical selected from the group consisting of azadirone, azadiradione, beta hydroxy azadiradione, and delta epi azadiradione.

22. The composition of claim 1, further comprising a bio-chemical selected from the group consisting of beta sitosterol, kaemferol, quercetin and myricetin.

* * * * *